(12) United States Patent
Fujieda

(10) Patent No.: US 6,190,011 B1
(45) Date of Patent: Feb. 20, 2001

(54) OPHTHALMIC APPARATUS AND A METHOD FOR STORING OPTHALMIC INFORMATION THEREFOR

(75) Inventor: Masanao Fujieda, Toyohashi (JP)

(73) Assignee: Nidek Co., Ltd. (JP)

(*) Notice: Under 35 U.S.C. 154(b), the term of this patent shall be extended for 0 days.

(21) Appl. No.: 09/258,294

(22) Filed: Feb. 26, 1999

(30) Foreign Application Priority Data

Feb. 27, 1998 (JP) .................................................. 10-064060

(51) Int. Cl.[7] .......................................................... A61B 3/14
(52) U.S. Cl. ................................................................ 351/206
(58) Field of Search ..................................... 351/200, 205, 351/206, 211, 212, 221; 708/141; 345/326

(56) References Cited

U.S. PATENT DOCUMENTS

| | | | |
|---|---|---|---|
| 4,199,816 | 4/1980 | Humphrey | 364/571 |
| 4,595,990 * | 6/1986 | Garwin et al. | 708/141 |
| 5,500,697 | 3/1996 | Fujieda | 351/212 |
| 5,841,511 | 11/1998 | D'Souza et al. | 351/212 |

FOREIGN PATENT DOCUMENTS

| | | |
|---|---|---|
| 64-5249 | 1/1980 | (JP) . |
| 9-234186 | 9/1987 | (JP) . |
| 7-124113 | 5/1995 | (JP) . |
| 8-504108 | 5/1996 | (JP) . |

* cited by examiner

Primary Examiner—George Manuel
(74) Attorney, Agent, or Firm—Finnegan, Henderson, Farabow, Garrett & Dunner

(57) ABSTRACT

An ophthalmic apparatus comprising a detecting device for detecting information of an eye to be examined, a first memory which is capable of storing a plurality of calibration information which is used for calibrating a result detected by the detecting device, and a second memory for storing the eye information, with associating the calibration information at the time of detecting with the eye information which is detected by the detecting device.

25 Claims, 4 Drawing Sheets

(CALIBRATION)

(PHOTOGRAPHY OF THE EYE TO BE EXMINED)

(ANALYSIS OF A CORNEAL SHAPE)

OPHTHALMIC APPARATUS AND A METHOD FOR STORING OPTHALMIC INFORMATION THEREFOR

BACKGROUND OF THE INVENTION

1. Field of the Invention

The present invention relates to an ophthalmic apparatus which obtains characteristics of an eye to be examined and a method for storing ophthalmic information therefor.

2. Description of Related Art

It is known for apparatuses which obtain characteristics of the eye to be examined, such as a corneal shape analyzing apparatus, a sectional view analyzing apparatus for analyzing a degree of opacities of a cornea or a crystalline lens and a shape of each part of an anterior part of the eye based on an image of a sectional view thereof.

For example, it is known for the corneal shape analyzing apparatus which projects a placido ring target onto a cornea, then photographing an image of the target by using a photographing camera, thereby calculating a curvature distribution over a wide range of the cornea, based on the obtained image data of the eye. The curvature distribution is visualized as the topography.

On calculating a corneal curvature, firstly, a plurality of standard balls having a known curvature are photographed whereby the image data are obtained. A calibration data is obtained based on the image data and the curvature of respective balls. Thereby, based on both of the calibration data and the image data of the eye, an analyzed result converted to an absolute value is calculated. The calibration data is intrinsic for the apparatus, therefore it is not shared by the same model apparatus due to the intrinsic difference. In the case of above mentioned corneal shape analyzing apparatus, the following are listed as the intrinsic difference: dispersion, displacement or the like of a placido ring, its mounting position and a photographing camera provided for a photographing optical system. The calibration data is used for the purpose that the analyzed result may not involve the intrinsic difference. The calibration data is usually stored in a memory of the apparatus in the form of a calibration data file.

Certainly, although the calibration data is intrinsic for the apparatus, if the obtained and analyzed result is stored, and the topography is re-displayed on another apparatus, then there is no difference between contents of displays.

In contrast, an apparatus which has a re-analysis function is known. The function is such as to store a raw image data of an eye which is obtained by using the photographing camera, then calling the raw image data and obtaining an analyzed result based on a calibration data.

However, referring to such apparatus that use calibration data as described above, there are problems as follows.

Firstly, such apparatus that stores only an analyzed result converted to an absolute value can not utilized for a new analyzing method. For example, in the case of examining variation of the analyzed result by way of obtaining results at a fixed period of time extending over a long period of time in order to carry out a historical observation, even if an operator makes an effort to interrupt the analysis and to adopt a new analyzing method, the operator can not use the new analyzing method with respect to such data as obtained in the past.

There is such possibility that an apparatus which has a function for storing a raw image data may adopt a new analyzing method by way of calling the raw image data, provided the identical apparatus is used. If the raw image data, obtained by using another apparatus, is analyzed by mistake, then reliability of the analyzed result is deteriorated due to the different calibration data. In addition, even if the identical apparatus is used, once the calibration data is changed by way of re-calibrating the apparatus, the re-analyzed result of the raw image data, obtained before or after calibration, can not achieve high accuracy.

SUMMARY OF THE INVENTION

The present invention has been made in view of the above circumstances and has an object to overcome the above problems and to provide an ophthalmic apparatus which can ensure the accuracy of the analyzed result with respect to each raw data. The raw data may be such as to be obtained by using different apparatus, or as to be obtained before and after re-calibration. In the specification, a raw data may be a raw data literally, a part of which may undergo image processing.

Another object of the present invention is to provide a method for storing an ophthalmic information therefor such as the raw data.

To achieve the objects and in accordance with the purpose of the present invention, as embodied and broadly described herein, an ophthalmic apparatus comprises detecting device for detecting information of an eye to be examined, first memory which is capable of storing a plurality of calibration information which is used for calibrating a result detected by the detecting device, and second memory for storing the eye information, and an associating device for associating the calibration information at the time of detection with the eye information which is detected by the detecting device.

The ophthalmic apparatus of the present invention may further comprise input device for inputting an analyzing program, and analyzing device for calculating or analyzing characteristics of the eye by using the eye information and the associated calibration information, based on the inputted analyzing program.

According to the present invention, the accuracy and the reliability of the analyzed result with respect to both of each raw data obtained by a different apparatus and each raw data obtained before and after re-calibration may be ensured.

Another aspect of the present invention is a method for storing an ophthalmic information utilized for an ophthalmic apparatus, the method comprising the steps of (1) detecting information of an eye to be examined, (2) obtaining calibration information which is used for calibrating a result detected by the detecting step, a plurality of the calibration information being capable of being stored, and (3) storing the eye information detected by the detecting step, and associating the calibration information at the time of detection eye information.

Further another aspect of the present invention is a, ophthalmic apparatus that comprises a projecting device for projecting a target pattern for measurement onto a cornea of an eye to be examined and a standard ball, photographing device for photographing an image of the target pattern for measurement, the image being formed onto the cornea and standard ball, calculating means for calculating calibration data based on image data and a curvature of the standard ball which is photographed by the photographing device, first memory which is capable of storing a plurality of the calibration data obtained by the calculating device, and second memory for storing image data of the eye, and an associating device for associating the calibration data at the time of photographing with the image data of the eye which is photographed by the photographing device.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
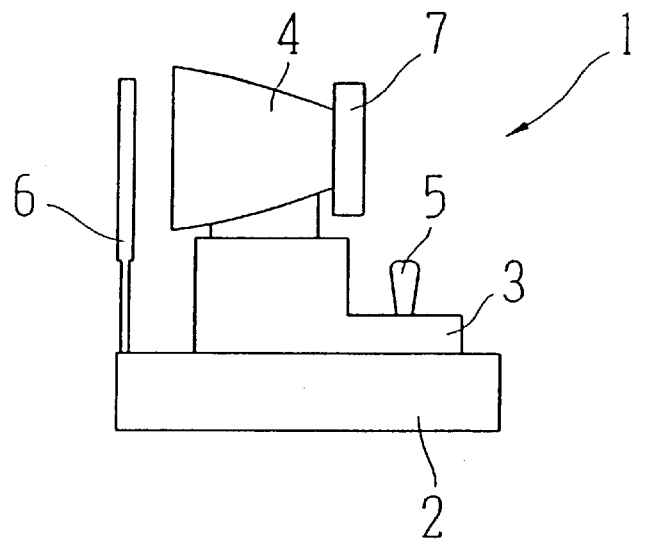
FIG. 1 is a side view of a main body of an apparatus for analyzing a corneal shape according to the preferred embodiment of the present invention.
Figure 2:
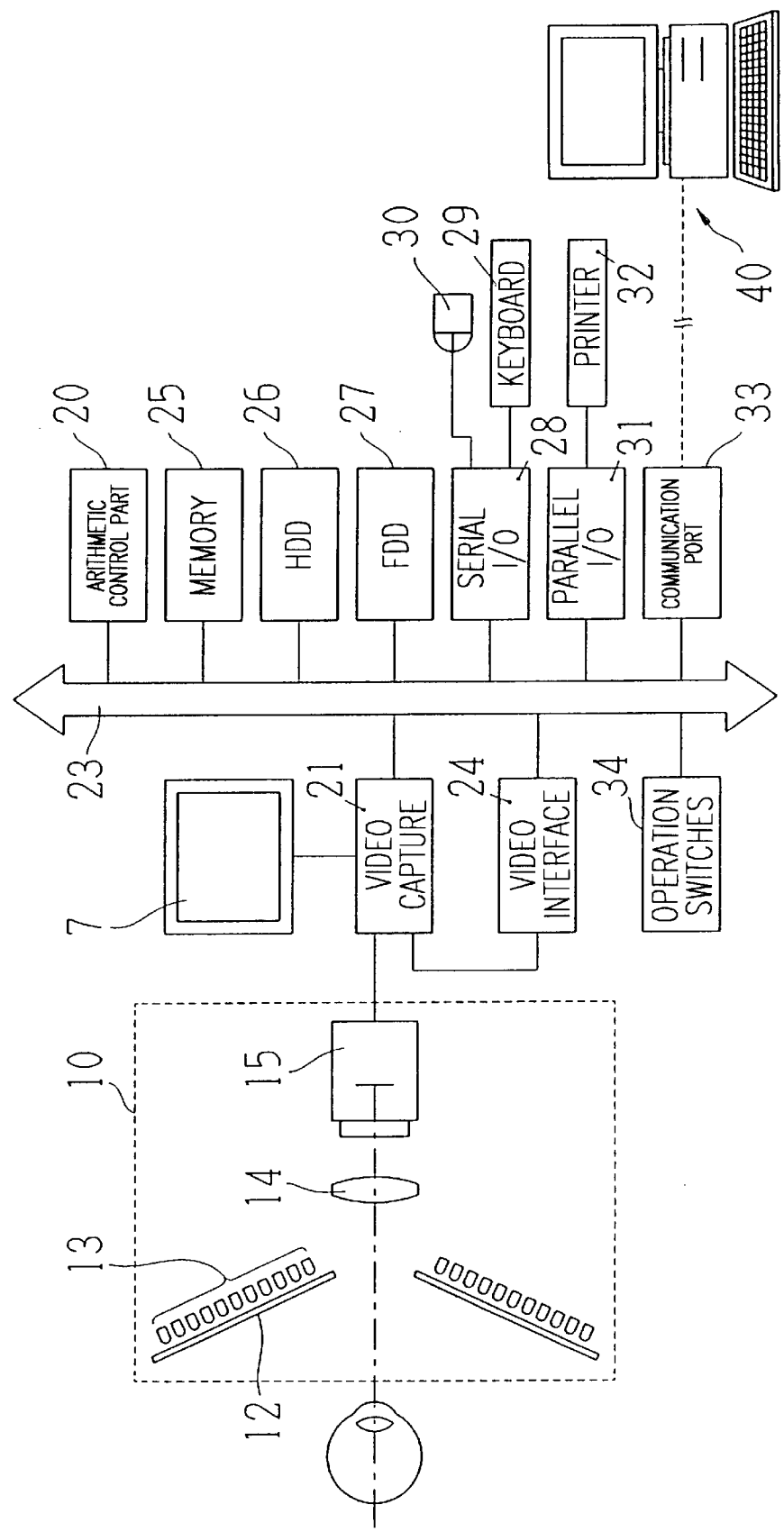
FIG. 2 is a view showing a schematic construction of a measuring optical system and a control system of the apparatus of the preferred embodiment of the present invention.

A detailed description of one preferred embodiment of the present invention will now be given referring to the accompanying drawings. FIG. 1 is a side view of the main body of the apparatus for analyzing a corneal shape according to the preferred embodiment of the present invention. FIG. 2 is a view showing a schematic construction of the measuring optical system and the control system of the apparatus.

In FIG. 1, a body 1 includes a fixation stand 2, a sliding plate 3 which can slide in the lateral and longitudinal directions, a measuring unit 4 which can move in the vertical direction relative to the sliding plate 3, a joystick 5 which is used for causing the sliding plate 3 and the measuring unit 4 to move, a face support unit 6 which is fixed to the fixation stand 2 and a liquid crystal display 7 having a color display and being disposed at an operator s side relative to the measuring unit 4.

In FIG. 2, numeral 10 denotes a measuring optical system which measures a corneal shape, being arranged in the measuring unit 4. The measuring optical system 10 includes a conic placido plate 12 on which a plurality of circular ring patterns are formed, an illumination light source 13 which illuminates the ring patterns of the placido plate 12 approximately uniformly, a photographing lens 14 and a CCD camera 15 which photograph images of the ring patterns projected on a cornea of an eye. The photographing lens 14 and the CCD camera 15 also act as an observation optical system by which an anterior part of the eye is observed. For the measuring unit 4, a fixation target optical system and an alignment optical system, which are not shown, Provided. Because are there is little relation with the present invention, the description is omitted.

The image photographed by the CCD camera 15 is captured by a video capture 21. The video capture 21 is connected to an arithmetic control part 20 via a data bus 23. The arithmetic control part 20 controls the whole of the apparatus and analyzes the images photographed by the CCD camera 15, and the like. In addition, a video interface 24 which generates a character, a figure and the like, a memory 25 which stores data temporally, a hard disk 26, a FDD (floppy disk drive) 27, a serial I/O 28 connected to both a keyboard 29 and a mouse 30, a parallel I/O 31 connected to a printer 32, a switch group 34 for operation, a communication port 33 and the like. An auxiliary storage and an external computer 40 are connected to the communication port 33, thereby enabling to send and receive data. Also, a telephone line and the like are enable to sending and receiving data with a remote location.

Figure 3A:
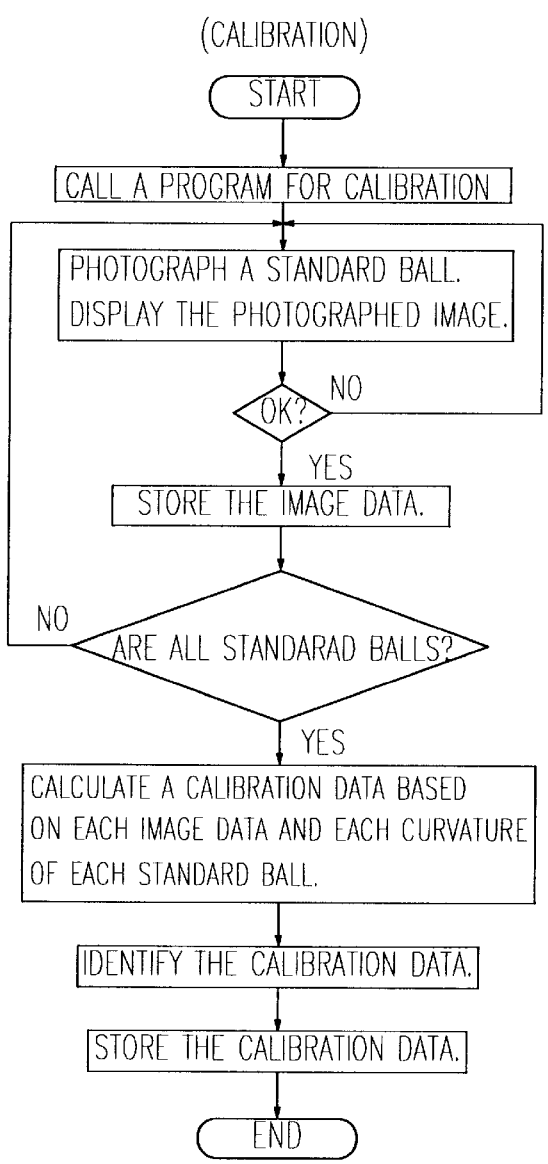
FIGS. 3A to 3C show flow charts for illustrating process of the apparatus for analyzing a corneal shape according to the preferred embodiment of the present invention.
Figure 3B:
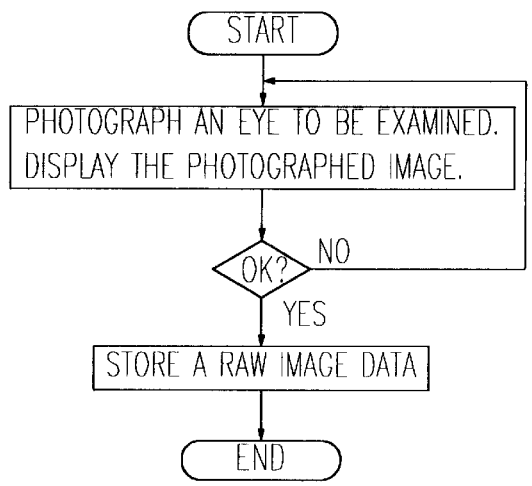
Figure 3C:
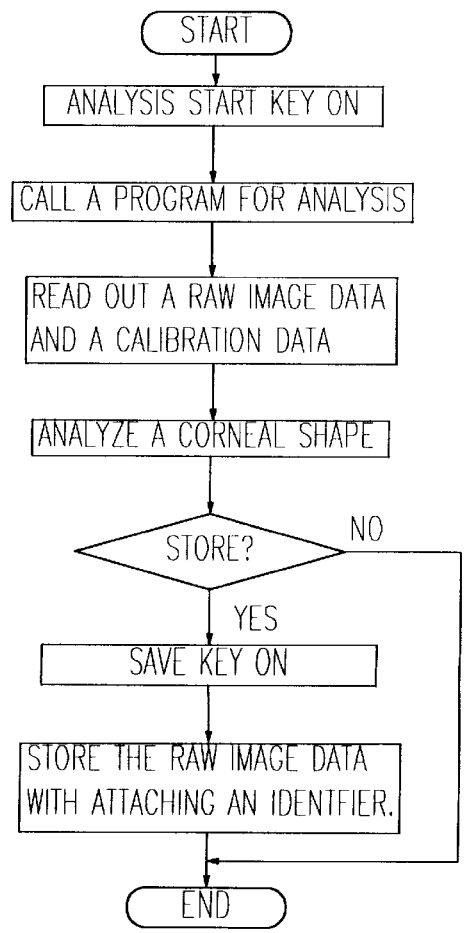

Next, the operation of the apparatus having the above described architecture will be described hereinafter with reference to FIGS. 3A to 3C. Firstly, the process of calibrating the apparatus will be described. The ring pattern of the placido plate 12 is projected onto a plurality of the standard balls having a known curvature. Then calibration data is calculated on the basis of both the image information at the time of photographing an image of the ring pattern formed on each ball and a curvature value of each ball.

Herein, a detail of this process will be described with reference to FIG. 3A. In response to the operation of the keyboard 29 and the mouse 30, a calibration program stored in the hard disk 26 is called. And with a fixation jig, the operator disposes one of the standard balls for calibration at the predetermined measuring position inside the face support unit 6 instead of disposing the eye thereat. Then the operator performs alignment of the measuring optical system 10. While aligning, the operator causes the sliding plate 3 and the measuring unit 4 to move so that an alignment target image may have the predetermined relationship with an alignment mark using the joystick 5 or the like. The operator observes both an image of the placido ring pattern and an image of an alignment target image which are displayed on the display 7.

After completing the alignment, the operator pushes a photographing switch in the switch group 34, thereby obtaining a photographing image. The image of the placido ring pattern photographed by the CCD camera 15 is captured by the video capture 21, being displayed on the display 7. If there is no problem in the displayed image, then the operator clicks a key "ACCEPT" displayed on the monitor with the mouse 30. Thereby the process of the calibration proceeds to the next step of photographing the remaining standard balls for calibration. The image data captured by the video capture 21 is transferred to and stored in the memory 25 or in the hard disk 26.

Similar to the above description, the operator photographs the remaining standard balls for calibration. After obtaining each image data of each standard ball, the arithmetic control part 20 calculates the relationship between each ring pattern image of each image data and each curvature of each standard ball, then calculates an intrinsic calibration data native to the apparatus thereupon. That is, the arithmetic control part 20 detects an edge of each ring pattern image formed on each standard ball, then calculates a distance between a center of a ring and each ring, where every meridian has a given angle, such as 1°, based on the edge position of each ring pattern image formed on each standard ball. The data obtained from this process for each standard ball is defined as a calibration data; more specifically, each calculated distance value of each ring pattern image formed on each standard ball is corresponded to a curvature of each standard ball, and other values between these distance values are calculated by means of interpolation. The calculated calibration data is stored in the hard disk 26.

Such calibration is performed when the apparatus is moved, or when the illumination light source 13 is changed to another one, or when the placido plate 12 is removed and re-mounted, or the like. Thereby dispersion and displacement of the optical systems and the like are corrected, thus accurate analyzed results are calculated. Preferably, the calibration may be performed at a fixed period of time such as a certain period of time or upon activation of the apparatus. A calibration data obtained by each calibration is controlled on the basis of date and time of the calibration, and is stored in the hard disk 26 as a calibration data file.

Next, the process of measuring the eye and storing the measured data will be described with reference to FIG. 3B and FIG. 3C. After fixing a face of the examine with the face support unit 6, the operator performs the alignment. On the display 7, an image of the ring pattern of the placido plate 12 is projected on the cornea of the eye, the eye is illuminated by the illumination light source 13. An alignment target image, an alignment mark and the like are displayed as is an image of the anterior portion of the eye. While observing them, the operator performs the alignment by moving the apparatus relative to the eye in a manner similar to the for the standard balls. After completing alignment, the operator pushes the photographing switch, then photographing an image of an anterior portion of the eye on which the placido ring pattern is projected. If there is no problem in the displayed image on the display 7, then the operator clicks a key "ACCEPT" displayed on the monitor with the mouse 30. Raw image data captured by the video capture 21 is stored in the memory 25 or in the hard disk 26.

Next, the process of analyzing a corneal shape will be described with reference to FIG. 3C. After obtaining the photographing image, once the operator clicks a key "ANALYSIS START" on the display 7, then an analysis program stored in the hard disk 26 is called and which analysis of a corneal shape is carried out. The arithmetic control part 20 reads out the raw image data which is photographed and stored, then calculates a distance between a center of a ring and each ring to which an edge process is given, every meridian per 1°, The process is similar to the manner of calculating the calibration data using the standard balls. Then, by comparing the distance of the raw image data with the calibration data, the arithmetic control part 20 obtains each corneal curvature at each position. Concerning calculation of a corneal curvature, refer to Japanese Patent Laid-Open No. HEI7-124113, corresponding to U.S. Pat. No. 5,500,697 disclosed by the present applicant. An analyzed result is displayed in the form of a color map, for example, topography.

Figure 4:
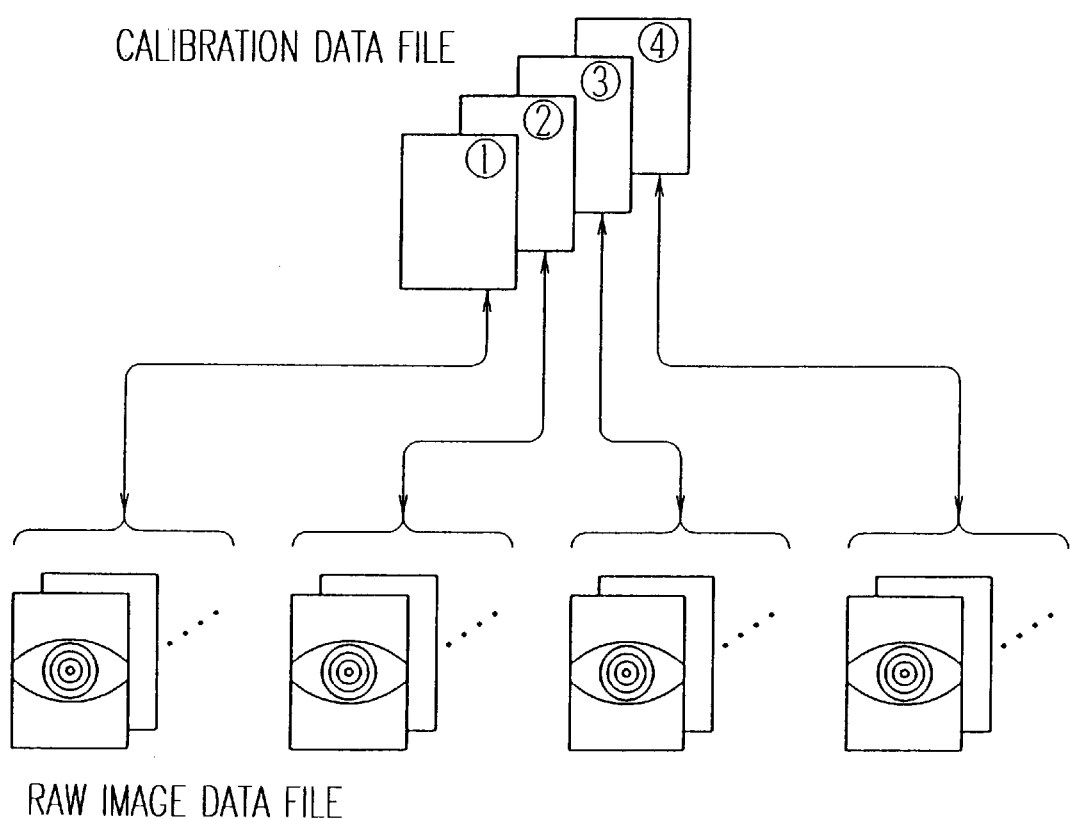
FIG. 4 is a view for illustrating a method for controlling a raw image data file and a calibration data file by binding of each identifier thereto.

In the case of storing the raw image data of and its analyzed result of the photographed image obtained as described above, the operator operates the mouse 30 or the like, then a picture for storing appears on the display 7. The operator then clicks a key "SAVE". The raw image data stored in the memory 25 is stored in the hard disk 26 and the calibration data is associated with the raw image data. The analyzed results such as a corneal curvature (strong and weak principal meridian curvatures, an axial power, a corneal cylindrical power), a non-spherical index and the like in the predetermined region of the eye are converted to the absolute values and then stored in the hard disk 26. The calibration data and the raw image data (and the analyzed results converted to the absolute value) can be stored as a set of these values. In order to save storage capacity, an identifier may be written in a raw image data file; the identifier denotes which calibration data file should be used for the raw image data file. Thereby, the raw image data file is associated with the calibration data file. More specifically, if numerous raw image data are stored by the identical apparatus for which calibration is performed several times while storing, then each identifier of each calibration data file is written in each raw image data file as shown in FIG. 4. In contrast, each associated identifier of each raw image data file may be bound to each calibration data file. As the name of an identifier both for a calibration data file and a raw image data file, for example, a time data, such as the date and the hour, while calibrating or photographing and the like, may be utilized.

More specifically, a raw image data (and an analyzed result) can be stored in a floppy disk by the FDD 27, or in an external storage connected via the communication port 33.

In this case, a necessary calibration data file is called from the hard disk 26, transferred and stored.

Figure 5:
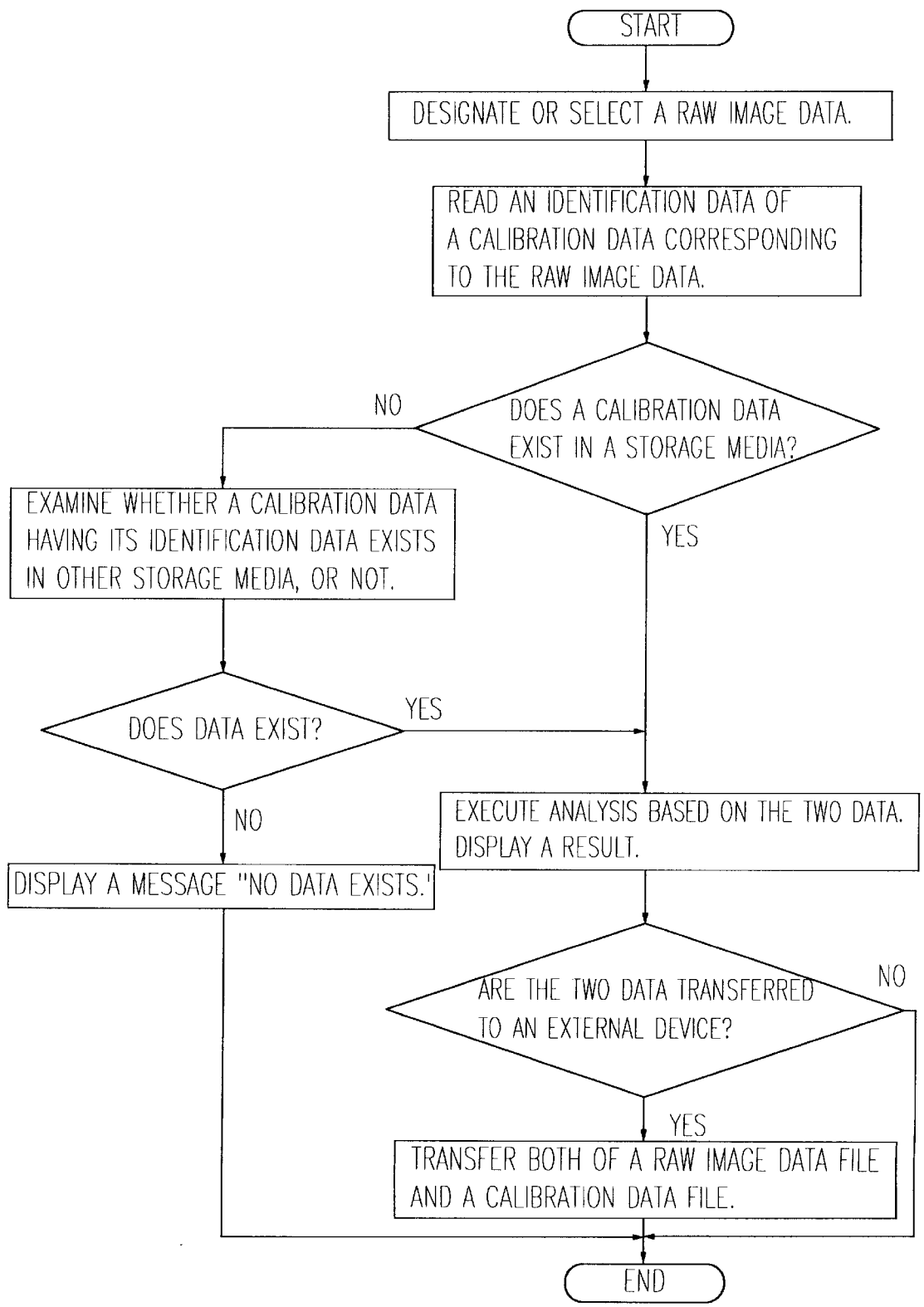
FIG. 5 shows a flow chart for re-analyzing a raw image data.

Next, re-analysis of the raw image data being stored will be described hereinafter (see the flow chart shown in FIG. 5). In the case of re-analysis of a raw image data having been stored in the past, after selecting a storage medium, such as a hard disk, a floppy disk or an external storage, in which a raw image data is stored, the operator designates a raw image data to be re-analyzed on the basis of data, such as ID number of an examine, a date of photography and the like. In this case, a search program stored in the apparatus can be utilized therefor. The arithmetic control unit 20 reads out the calibration data corresponding to the designated raw image data. If there is no calibration data corresponding to the selected storage medium, then another storage medium is also examined. If two data files are read out, then the arithmetic control unit 20 performs the predetermined analysis based on the two data files, displaying the analyzed result on the display 7.

As described above, by performing the analysis in a manner of calling the calibration data corresponding to the raw image data, even if a corneal shape analyzing apparatus is re-calibrated, then an accurate analyzed-result can be obtained. The accurate analyzed-result is such as to reflect the calibration data at the time when the raw image data was obtained. In addition, in the case that an analyzing program is changed to another program, such as the more accurate method of an edge-process for a raw image data or the more progressive analyzing program, the method and program may be applied to a raw image data having been photographed in the past. Further, various applications may be considered in the future.

In the case of transferring data to an analyzing apparatus, such as the external computer 40 having an analyzing program or the like, a set of a raw image data and a calibration data are made to be outputted and transferred simultaneously. Accordingly, even if the apparatus has no raw image data, then the analyzed results can be calculated by using the other analyzing apparatus. In addition, accurate analysis can be performed for the data obtained by another corneal shape analyzing apparatus.

Further, by using another analyzing apparatus, alternative applications can be realized. For example, an analyzing apparatus, installed in a general ophthalmologist, calculates an easy analyzing-item. In contrast, an analyzing apparatus, being installed in a special hospital and having an advanced program may calculate an advanced analyzing-item. That is, by transferring the files both of a raw image data and a calibration data (it may be in a form of a floppy disk or a data communication via a telephone circuit), a more precise analyzing result is to be calculated by the special hospital. This system enables the general ophthalmologist to ask for a detailed diagnosis from a specialist.

In addition, a system adopted for the analyzing apparatus installed in the general ophthalmologist office may be limited to only necessary contents, thus allowing to save cost of an apparatus. Therefore, the advanced analyzing program, being high-priced, may be installed only in the special hospital. A manufacturer can reduce costs by way of separating the program from the apparatus. This separation is also economical for users because they get a complete suite of the apparatus which satisfies the purpose.

Above description is made by adopting the corneal shape analyzing apparatus as an example. Alternatively, in the case of an apparatus for analyzing a section of an anterior portion of the eye, the present invention may be applied as follows. In a periphery of a photographed image, distortion is generated by a lens system in a sectional photographing optical system. If a grid chart, being accurate as a calibration data, is photographed in advance, then an accurate size of each part of the photographed section can be obtained in a manner of performing calibration for the photographed image although there is distortion at a periphery of the image. If a calibration data obtained for every calibration is stored and a set of the sectional photographed image and the calibration data (being associated with each other) is stored, then an accurate result is obtained at all times even if the image has been photographed in the past or photographed by a different apparatus.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It intended that the scope of the invention be defined by the claims appended hereto, and their equivalents.

What is claimed is:

1. An ophthalmic apparatus comprising:
   a detecting device having a detecting system for detecting eye information of an eye to be examined;
   a first memory configured to store calibration information used for calibrating dispersion or displacement of the detecting system;
   a second memory configured to store the eye information; and
   an associating device for associating the calibration information with the eye information at the time of detection of the eye information.

2. The ophthalmic apparatus according to claim 1, further comprising an analyzing device for analyzing characteristics of the eye based on the eye information and the calibration information associated with the eye information.

3. The ophthalmic apparatus according to claim 1, wherein the associating device further comprises a binding device for binding an identifier to the eye information and the calibration information at the time of detection of the eye information.

4. The ophthalmic apparatus according to claim 1, wherein the first memory stores a plurality of the calibration information, and the second memory stores a plurality of the eye information, the apparatus further comprising:
   a designating device for designating one of the plurality of the eye information stored in the second memory; and
   a reading device for reading out one of the plurality of the calibration information from the first memory based on the eye information associated with the calibration information and designated by the designating device.

5. The ophthalmic apparatus according to claim 1, further comprising a calculating device for obtaining the calibration information.

6. The ophthalmic apparatus according to claim 1, further comprising a sending and receiving device for sending and receiving a set of the eye information and the calibration information associated with the eye information to and from an external device.

7. The ophthalmic apparatus according to claim 1, further comprising:
   a first casing housing the detecting device, wherein the detecting device detects the eye information;
   a second casing housing the second memory; and
   a sending device for sending the eye information from the detecting device to the second memory.

8. The ophthalmic apparatus according to claim 7, further comprising a calculating device for obtaining the calibration information, wherein the first casing further houses the calculating device, the second casing further houses the first memory, and the sending device further sends the calibration information from the calculating device to the first memory.

9. The ophthalmic apparatus according to claim 1, wherein the detecting device further comprises a photographing device having a photographing system for photographing an image of a target for measurement formed on the eye, the calibration information used for calibrating dispersion or displacement of the photographing system, and the eye information including the image of the target for measurement.

10. The ophthalmic apparatus according to claim 9, further comprising a projecting device for projecting the target for measurement onto the eye.

11. The ophthalmic apparatus according to claim 1, further comprising:
    an input device for inputting an analyzing program; and
    an analyzing device for calculating or analyzing characteristics of the eye based on the eye information and the calibration information associated with the eye information in accordance with the inputted analyzing program.

12. A method for storing ophthalmic information utilized for an ophthalmic apparatus, the method comprising the steps of:
    detecting eye information of an eye to be examined;
    obtaining calibration information used for calibrating dispersion or displacement of a detecting system which detects the eye information
    associating the eye information with the calibration information at the time of detection of the eye information;
    storing the calibration information; and
    storing the eye information associated with the calibration information at the time of detection of the eye information.

13. The method according to claim 12, wherein the step of associating further comprises the step of binding an identifier to the eye information and the calibration information at the time of detection of the eye information.

14. An ophthalmic apparatus comprising:
    a projecting device for projecting a target pattern for measurement onto a cornea of an eye to be examined and a standard ball;
    a photographing device for photographing an image of the target pattern formed on the cornea for measurement and an image of the target pattern formed on the standard ball for measurement;

a calculating device for obtaining calibration data based on the image formed on the standard ball and a curvature of the standard ball;

a first memory configured to store the calibration data; and a second memory configured to store data on the image formed on the cornea.

15. The ophthalmic apparatus according to claim 14, further comprising an analyzing device for analyzing characteristics of the eye based on the data on the image formed on the cornea and the calibration data.

16. The ophthalmic apparatus according to claim 14, further comprising an associating device for associating the data on the image formed on the cornea with the calibration data at the time of photographing of the image formed on the cornea.

17. The ophthalmic apparatus according to claim 16, wherein the first memory stores a plurality of the calibration data and the second memory stores a plurality of the data on the image formed on the cornea, the apparatus further comprising:

a designating device for designating one of the plurality of the data on the image formed on the cornea stored in the second memory; and a reading device for reading out one of the plurality of the calibration data from the first memory based on the data on the image formed on the cornea that is associated with the calibration data and is designated by the designating device.

18. The ophthalmic apparatus according to claim 16, further comprising a sending and receiving device for sending and receiving a set of the data on the image formed on the cornea and the calibration data associated with the data on the image formed on the cornea to and from an external device.

19. The ophthalmic apparatus according to claim 16, wherein the associating device further comprises a binding device for binding an identifier to the data on the image formed on the cornea with the calibration data at the time of photographing the image formed on the cornea.

20. An ophthalmic apparatus comprising:

photographing means having a photographing optical system for photographing an image of an eye to be examined;

first storing means for storing calibration information used for calibrating dispersion or displacement of the photographing optical system;

second storing means for storing data on the image;

associating means for associating the data on the image with the calibration information at the time of photographing of the image; and program storing means for storing a program for obtaining characteristics of the eye based on the data on the image and the calibration information.

21. The ophthalmic apparatus according to claim 20, further comprising analyzing means for analyzing the characteristics of the eye based on the data on the image and the calibration information that is associated with the data on the image in accordance with the program stored.

22. The ophthalmic apparatus according to claim 20, wherein the associating means further comprises binding means for binding an identifier to the data on the image and the calibration information at the time of photographing the image.

23. The ophthalmic apparatus according to claim 20, wherein the first storing means stores a plurality of the calibration information, and the second storing means stores a plurality of the data on the image, the apparatus further comprising:

designating means for designating one of the plurality of the data on the image stored in the second storing means;

reading means for reading out one or more of the plurality of the calibration information from the first storing means based on the data on the image associated with the calibration information and designated by the designating device.

24. The ophthalmic apparatus according to claim 20, further comprising calculating means for obtaining the calibration information.

25. The ophthalmic apparatus according to claim 20, further comprising sending and receiving means for sending and receiving a set of the data on the image and the calibration information associated with the data on the image to and from an external device.

\* \* \* \* \*

UNITED STATES PATENT AND TRADEMARK OFFICE
CERTIFICATE OF CORRECTION

PATENT NO. : 6,190,011 B1
DATED : February 20, 2001
INVENTOR(S) : Fujieda

It is certified that error appears in the above-identified patent and that said Letters Patent is hereby corrected as shown below:

On the Title Page, Item (54), in the Title, line 2, "OPTHALMIC" should read

--OPHTHALMIC-- (second occurrence).

Signed and Sealed this

Fifth Day of June, 2001

Attest:

*Attesting Officer*

NICHOLAS P. GODICI
*Acting Director of the United States Patent and Trademark Office*